United States Patent [19]

DeLuca et al.

[11] 4,338,312
[45] Jul. 6, 1982

[54] METHOD FOR PREVENTING PARTURIENT PARESIS IN DAIRY CATTLE

[75] Inventors: Hector F. DeLuca; Heinrich K. Schnoes, both of Madison; Neal A. Jorgensen, Middleton, all of Wis.

[73] Assignee: Wisconsin Alumni Research Foundation, Madison, Wis.

[21] Appl. No.: 262,093

[22] Filed: May 11, 1981

[51] Int. Cl.³ .................. A01N 45/00; A61K 31/59
[52] U.S. Cl. .............................. 424/236; 260/397.2
[58] Field of Search .................... 424/236; 260/397.2

[56] References Cited

U.S. PATENT DOCUMENTS 3,879,548  4/1975  DeLuca et al. .................... 424/236
4,110,446  8/1978  DeLuca et al. .................... 424/236

Primary Examiner—Elbert L. Roberts
Attorney, Agent, or Firm—Howard W. Bremer

[57] ABSTRACT

A method for prophylactically treating dairy cattle for parturient paresis by administering to the cattle a 25-hydroxylated vitamin D compound and a 1α-hydroxylated vitamin D compound in combination in an amount sufficient to induce said prophylaxsis.

11 Claims, No Drawings

METHOD FOR PREVENTING PARTURIENT PARESIS IN DAIRY CATTLE

The invention described herein was made in the course of work under a grant or award from the Department of Health and Human Services.

This invention relates to a method for prophylactically treating dairy cattle for parturient paresis using a mixture of 25-hydroxycholecalciferol and 1α-hydroxycholecalciferol.

Parturient paresis (milk fever) is a metabolic disease of dairy cows wherein severe hypocalcemia, resulting from parturition and the initial formation of milk, leads to a disorder characterized by the cow's inability to command use of their muscles and a placid, immobile appearance.

The disease is manifested by a decrease in plasma calcium, usually between six to thirty hours after parturition, to a value so low as to induce tetany with resultant immobilization of the cow. There is also generally an accompanying decrease in the blood phosphate level. As an example, the plasma calcium level in a cow prior to calving is about 10 mg./100 ml. (or 10 mg. percent). Following parturition this level will normally dip to about 7-8 mg. percent but will then rise in a reasonable time to the more normal 10 mg. percent range. In a cow afflicted with milk fever, however, after parturition the plasma calcium may dip more drastically, such as into the 5 mg. percent range, and it is recognized that at such plasma calcium levels the cow can go into tetany and a condition known as Downer's Syndrome.

Such low plasma calcium levels are not necessary in all cases to induce milk fever disease and the disease is experienced at substantially higher calcium levels depending upon the individual animal involved. If treatment for such condition is not however, immediate and successful there is a real danger that the cow may die or be afflicted with a lasting paralysis, or at the very least that its milk production will be substantially decreased. (See "Milk Fever Causes, Methods of Treatment and Prevention," S. H. Morrison, Vol. 1, No. 2, a publication of Borden Chemical Company and J. M. Payne, Brit. Vet. Assn. "Recent Advances in Our Knowledge of Milk Fever," presented at 87th Annual Congress of the Association, Sept. 6, 1964).

The incidence of milk fever disease has been estimated to be in the range from about 3.5-5% of the world's dairy cows. In individual herds, however, the incidence may be as high as 60-70%. It appears that the incidence of the disease is highest among high milk producing cows during the third and later lactation periods although at times it has been observed in the second lactation period. In any event, once a cow has had milk fever there is an 80-90% probability that she will again be so afflicted after her next parturition. As a consequence, there has been much interest in developing procedures for preventing this disorder.

For example, feeding of a low calcium diet or feeding a high phosphate in a grain ration, which is tantamount to a low calcium diet, has been suggested as a preventative for the disease. Since, however, it is necessary to feed cattle a high calcium diet during their non-lactating periods to replenish the calcium stores depleted by previous milking such treatment is not a very practical solution for milk fever problem. Other methods of treatment suggested include air inflation of the udder—a treatment not used because of the danger of mastitis and other infection—and acidification of silage which alleviated the disease. This latter method is impractical because of problems engendered by the acid intake. Hibbs and co-workers (Hibbs, J. W. and Conrad, H. R., J. Dairy Science 49, 243, 1966) were the first to use very large doses of vitamin D to reduce the incidence of parturient paresis and currently the most widely used treatment for milk fever is the administration of vitamin D in massive dosage. For example, in one method the cow is fed 20 million units per day of vitamin D for three to seven days before calving while in another method 10 million units of vitamin D is injected intramuscularly before calving. Although these methods are of value they are associated with potentially high risk and other disadvantages. With administration of such large dosages of vitamin D there is a real danger of vitamin D toxicity and, as a consequence, death of the cow or damage through abnormal calcification of the soft tissues such as the kidney, aorta, etc. Even if the animal survives without damage the milk produced may not be fit for human or calf consumption for some time because of the high content of vitamin D in the milk. Furthermore, the unpredictability of the calving date places an added difficulty on the farmer as to when the vitamin D dosage should be given. If the vitamin D dosage is given too far in advance the incidence of milk fever disease is actually increased by the treatment.

Other methods which have been suggested for combatting milk fever disease utilize the administration of 25-hydroxycholecalciferol (U.S. Pat. No. 3,646,203, issued Feb. 29, 1972), 1α-hydroxycholecalciferol (U.S. Pat. No. 3,879,548), and 1,25-dihydroxycholecalciferol (U.S. Pat. No. 4,110,446).

That 25-hydroxyvitamin $D_3$ (25-OH-$D_3$) can markedly reduce the incidence of parturient paresis will be evident from the following table although it should also be observed that 25-OH-$D_3$ does not eliminate or totally prevent the disorder.

TABLE 1

| Efficacy of 25-OH—$D_3$ in Prevention of Parturient Paresis | | | |
|---|---|---|---|
| Dose* mg | Total Cows Treated | Milk Fever | Incidence % |
| 0 | 175 | 75 | 43 |
| 2 | 27 | 4 | 15 |
| 4 | 173 | 18 | 10 |

*The dose was dissolved in 5 ml corn oil and injected intramuscularly every 7 days beginning 7 days before predicted calving date.

It is evident from the above data that the preferred dose would be 4 mg. of 25-OH-$D_3$ to achieve the lowest incidence of the disease.

In like fashion 1α-hydroxycholecalciferol (1α-OH-$D_3$) is also capable of reducing the incidence of parturient paresis as will be evident from the following table.

TABLE 2

| Efficacy of 1α-OH—$D_3$ in Prevention of Parturient Paresis | | | |
|---|---|---|---|
| Dose* mg | Total Cows Treated | Milk Fever | Incidence % |
| 0 | 26 | 8 | 31 |
| 0.3 | 6 | 1 | 16 |
| 0.5 | 10 | 2 | 20 |

*The dose was dissolved in 5 ml. corn oil and injected as in Table 1.

It should be observed from the above data that, as with the use of 25-OH-$D_3$, treatment with 1α-OH-$D_3$, although substantially decreasing the incidence of the disease does not totally prevent it.

It has now been found, however, that if 25-OH-D$_3$ and 1α-OH-D$_3$ are used in combination in treating dairy cows with a view toward preventing parturient paresis, the combination of compounds appears to afford complete protection against the disease as will be apparent from the following Example which is intended to be illustrative only. Since it is the consensus in the industry that high-producing cows, generally beginning with the third lactation, are most susceptible to parturient paresis, only such animals were used for evaluation.

EXAMPLE

Third lactation or better Holstein cows (a high producing strain) were fed a diet in the dry period of high calcium and low phosphorus. This diet was also maintained throughout the parturition portion of the experiment. One-half of the cows randomly selected remained untreated whereas the remainder received 0.5 mg. of 1α-OH-D$_3$ and 4 mg. of 25-OH-D$_3$ dissolved in 5 ml of corn oil intramuscularly at least 7 days before the predicted calving date. The cows were reinjected with the same preparation every seventh day for a period of 3 weeks. Upon successful calving, treatment was discontinued. Results are shown in Table 3 below.

TABLE 3

Efficacy of 25-OH—D$_3$ (4 mg.) plus 1α-OH—D$_3$ (0.5 mg.) in Preventing Parturient Paresis

| Group | Number of Cows | | | |
|---|---|---|---|---|
| | Total | Normal | Paretic | Incidence |
| Untreated | 23 | 15 | 8 | 34.8% |
| Treated* | 22 | 22 | 0 | 0% |

*Maximum of 3 injections given. Any cow treated not calving within 7 days from last injection was removed from the trial. This occurred with 2 cows, one of which developed parturient paresis, the other of which was normal.

It is obvious from the foregoing data that dairy cows treated with the combination of 25-OH-D$_3$ and 1α-OH-D$_3$ were most unexpectedly, afforded complete protection from parturient paresis. This strongly suggests that the combination of any 25-hydroxylated form of vitamin D with any 1α-hydroxylated form of that vitamin would provide an unexpectedly effective means for preventing parturient paresis.

Effective and practical administration of the combination of 25-OH-D$_3$ and 1α-OH-D$_3$, or, more broadly, the combination of a 25-hydroxylated form of vitamin D with a 1α-hydroxylated form of vitamin D can be accomplished by injection of the material intravenously, intramuscularly or subcutaneously while dissolved in a suitable vehicle such as an innocuous oil or propylene glycol. Alternatively, the combination of 25-OH-D$_3$ and 1α-OH-D$_3$ can be compounded with other materials to form a bolus, or can be encapsulated, so that oral administration can be the preferred route of administration. Or, if desired the materials can be applied topically in a suitable vehicle and perhaps in the presence of an agent e.g. dimethyl-sulfoxide, which enhances penetration of the skin.

Although the dosages in the foregoing Example are effective in providing total protection against parturient paresis, the particular dosages, or ratios of 25-OH-D$_3$ to 1α-OH-D$_3$ specified are not necessarily critical, other dosages, as well as ratios, of the combination of these compounds being equally effective. Dosage can, of course, vary with the size of the cow to which it is being administered. In any event, sufficient of the combination in effective ratios of one to the other must be given to accomplish the desired end, namely, complete protection against the incidence of parturient paresis. The use of more than sufficient material to accomplish such end should be avoided as an economically unsound practice.

We claim:

1. The method for prophylactically treating dairy cattle for parturient paresis which comprises administering to the cattle a combination of a 25-hydroxylated form of vitamin D and a 1α-hydroxylated form of vitamin D in an amount sufficient to induce said prophylaxsis.

2. The method of claim 1 wherein the 25-hydroxylated form of vitamin D and 1α-hydroxylated form of vitamin D are administered in the ratio of 8:1.

3. The method of claims 1 or 2 wherein the 25-hydroxylated form of vitamin D and the 1α-hydroxylated form of vitamin D are respectively 25-hydroxy vitamin D$_3$ and 1α-hydroxy vitamin D$_3$.

4. The method of claim 3 wherein the 25-hydroxy vitamin D$_3$ and 1α-hydroxylated vitamin D$_3$ are administered in respective amounts of 4 milligrams and 0.5 milligrams in an innocuous carrier.

5. The method of claim 4 where the administration is accomplished at least seven days prior to predicted calving date.

6. The method of claim 1 wherein the treatment is by injection.

7. The method of claim 6 wherein the injection is intramuscular.

8. The method of claim 6 wherein the injection is subcutaneous.

9. The method of claim 6 wherein the injection is intravenous.

10. The method of claim 1 wherein the treatment is oral.

11. The method of claim 1 wherein the treament is topical.

* * * * *